United States Patent
Schleuter et al.

(10) Patent No.: US 10,444,128 B2
(45) Date of Patent: Oct. 15, 2019

(54) LOAD PATH STATUS DETECTION SYSTEM

(71) Applicant: The Boeing Company, Chicago, IL (US)

(72) Inventors: Lisa G. Schleuter, Mukilteo, WA (US); Bret Alan Bowers, Freeland, WA (US)

(73) Assignee: The Boeing Company, Chicago, IL (US)

( * ) Notice: Subject to any disclaimer, the term of this patent is extended or adjusted under 35 U.S.C. 154(b) by 162 days.

(21) Appl. No.: 15/289,310

(22) Filed: Oct. 10, 2016

(65) Prior Publication Data

US 2018/0100790 A1  Apr. 12, 2018

(51) Int. Cl.
| | |
|---|---|
| *G01N 3/08* | (2006.01) |
| *G01L 1/12* | (2006.01) |
| *G01L 1/22* | (2006.01) |
| *B64C 9/02* | (2006.01) |
| *B64D 45/00* | (2006.01) |

(52) U.S. Cl.
CPC ............... *G01N 3/08* (2013.01); *B64C 9/02* (2013.01); *G01L 1/127* (2013.01); *G01L 1/2287* (2013.01); *B64D 2045/0085* (2013.01); *Y02T 50/44* (2013.01)

(58) Field of Classification Search
CPC . G01L 1/12; G01L 1/27; G01L 1/2287; G01L 1/122; G01L 1/127; G05D 1/00; G01N 3/08; G01N 2203/005; G06F 19/00; F16D 9/06; B64C 13/00; B64C 13/38; B64C 13/50; F16H 57/01
USPC .................................................. 73/777, 779
See application file for complete search history.

(56) References Cited

U.S. PATENT DOCUMENTS

| | | | | |
|---|---|---|---|---|
| 4,435,100 A | * | 3/1984 | Cox | F16B 31/00 16/378 |
| 4,649,484 A | * | 3/1987 | Herzog | B64C 13/503 244/194 |
| 8,033,500 B1 | * | 10/2011 | Charafeddine | B64C 13/42 244/75.1 |
| 8,457,836 B2 | * | 6/2013 | Balasu | B60T 17/221 244/118.5 |
| 8,702,034 B2 | * | 4/2014 | Moulon | B64C 13/28 244/99.2 |
| 8,820,172 B2 | * | 9/2014 | Bouillot | B64C 9/02 73/761 |
| 9,868,514 B2 | * | 1/2018 | Schievelbusch et al. | B64C 13/28 244/99.3 |
| 10,065,728 B2 | * | 9/2018 | Cyrot | B64C 13/28 244/99.4 |

(Continued)

OTHER PUBLICATIONS

Schleuter et al., "Fastener Status Detection System," U.S. Appl. No. 15/137,366, filed Apr. 25, 2016, 34 pages.

*Primary Examiner* — Octavia Hollington
(74) *Attorney, Agent, or Firm* — Yee & Associates, P.C.

(57) ABSTRACT

A load path status detection system comprising a primary fastener, a load sensor, a primary structural link, and a secondary structural link. The primary fastener extends through the primary structural link. The load sensor is associated with the primary structural link. The primary structural link carries a load when a primary load path, formed by the primary fastener and the primary structural link, is functioning. The secondary structural link is parallel to the primary structural link, wherein the secondary structural link does not carry a load when the primary load path is functioning.

19 Claims, 6 Drawing Sheets

(56) References Cited

U.S. PATENT DOCUMENTS

| | | | |
|---|---|---|---|
| 10,132,724 B2* | 11/2018 | Moulon et al. | G01M 99/008 244/99.3 |
| 2013/0001357 A1* | 1/2013 | Cyrot | B64C 13/28 244/99.4 |
| 2016/0304188 A1* | 10/2016 | Moulon | G01M 99/008 |
| 2017/0305529 A1* | 10/2017 | Schleuter | G01L 5/0047 |

* cited by examiner

LOAD PATH STATUS DETECTION SYSTEM

BACKGROUND INFORMATION

1. Field

The present disclosure relates generally to load paths, and in particular, to primary load paths having backups. Still more particularly, the present disclosure relates to a status detection system for a load path.

2. Background

Load paths transfer load between or within components. In joints, a load path may comprise a fastener and a structural link. Some load paths may be redundant. For example, backup, or secondary, load paths will be formed near primary load paths. In the event that a primary load path stops functioning, the secondary load path will act to transfer load between components.

Detecting a broken fastener or structural link is often more difficult than desired. For example, some fasteners are positioned within large platforms and hidden from view. As another example, even when a load path is visible, a break within the primary structural component may not be visible. Therefore, it would be desirable to have a method and apparatus that takes into account at least some of the issues discussed above, as well as other possible issues.

SUMMARY

In one illustrative embodiment, a load path status detection system is presented. The load path status detection system comprises a primary fastener, a load sensor, a primary structural link, and a secondary structural link. The primary fastener extends through a primary structural link. The load sensor is associated with the primary structural link. The primary structural link carries a load when a primary load path formed by the primary fastener and the primary structural link is functioning. The secondary structural link is parallel to the primary structural link, wherein the secondary structural link does not carry a load when the primary load path is functioning.

In another illustrative embodiment, a method is presented. A primary structural link is connected to a first component using a primary fastener to form a primary load path. A measurement is generated using a load sensor associated with the primary structural link. Whether the primary load path is functioning is determined using the measurement.

In yet another illustrative embodiment, an assembly is presented. The assembly comprises a first component, a second component, and a sensor. The first component is connected to a primary structural link using a primary fastener and is connected to a pair of secondary structural links using a pair of secondary fasteners. The second component is connected to the primary structural link using a connector. The sensor is associated with the primary structural link and configured to measure a load on the primary structural link.

The features and functions can be achieved independently in various embodiments of the present disclosure or may be combined in yet other embodiments, in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives, and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account one or more different considerations. For example, the illustrative embodiments recognize and take into account that flight control and high lift surfaces on an aircraft are used to maneuver and control the altitude of an aircraft. High lift surfaces are used to generate additional lift at low speeds.

An aircraft may have many types of flight control and high lift surfaces. These surfaces include but are not limited to, for example, ailerons, elevators, rudders, spoilers, flaps, slats, airbrakes, and other suitable control and high lift surfaces. Flight control and high lift surfaces may be driven between an extended and a retracted position using an actuator system.

The illustrative embodiments recognize and take into account that control and high lift surface systems often have dual load paths as a failsafe. For example, currently dual pins are used in primary flap supports. The illustrative embodiments recognize and take into account that current detection methods may be undesirably heavy. Further, the illustrative embodiments recognize and take into account that current detection methods may be undesirably unreliable. Specifically, current detection methods include mechanical methods that may be affected by external weather, debris, and reliability of the mechanical components.

For example, currently a spring loaded door may be activated to warn of a pin failure on a primary flap support. However, the door may be less visible or less reliable than desired. Further, the illustrative embodiments recognize and take into account that there is no secondary system to determine whether the spring loaded door has been inadvertently activated.

Figure 1:
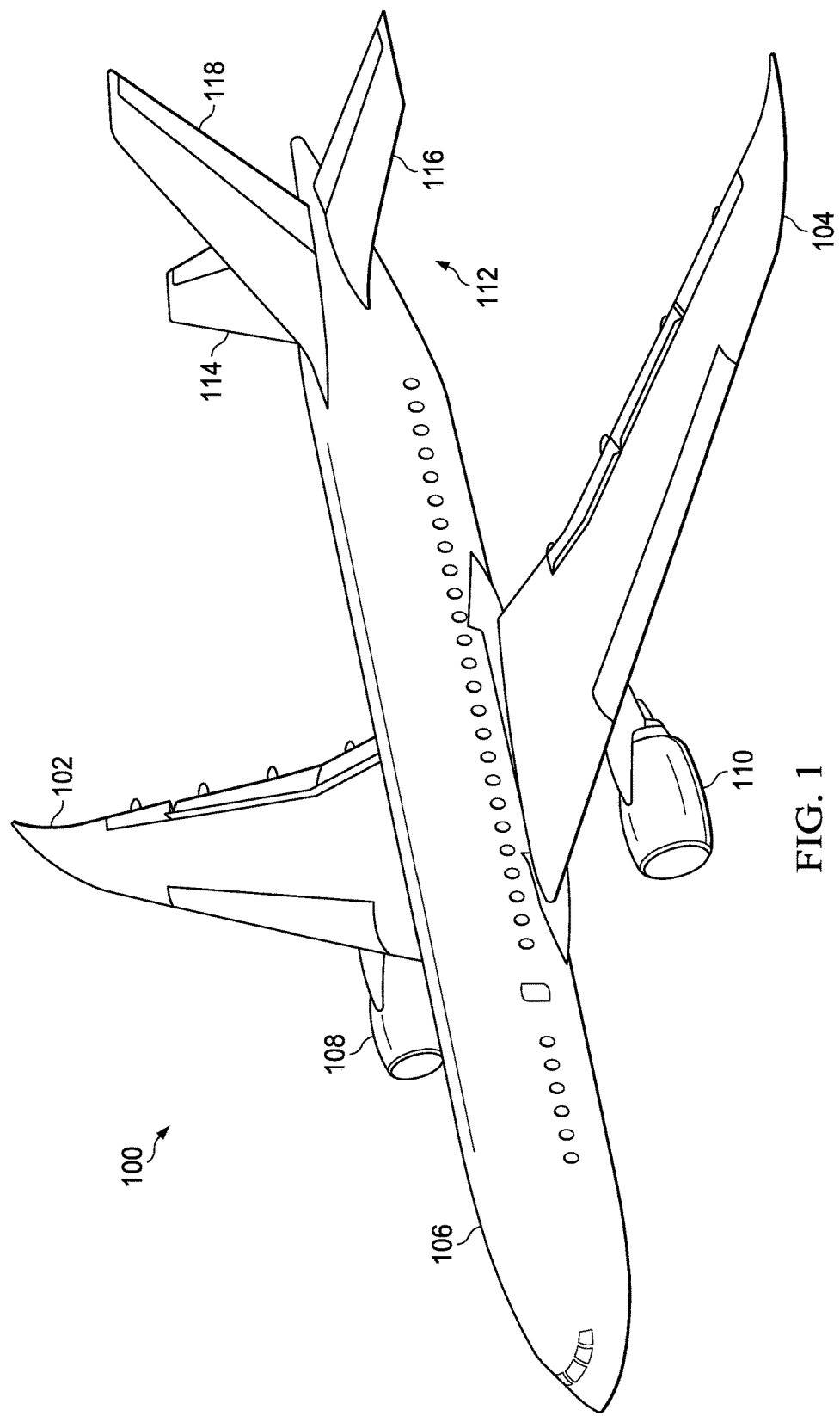
FIG. 1 is an illustration of an aircraft in which an illustrative embodiment may be implemented.

With reference now to the figures, and in particular, with reference to FIG. 1, an illustration of an aircraft is depicted in which an illustrative embodiment may be implemented. In this illustrative example, aircraft 100 has wing 102 and wing 104 attached to body 106. Aircraft 100 includes engine 108 attached to wing 102 and engine 110 attached to wing 104. Body 106 has tail section 112. Horizontal stabilizer 114, horizontal stabilizer 116, and vertical stabilizer 118 are attached to tail section 112 of body 106.

Aircraft 100 is an example of an aircraft having a load path status detection system in accordance with an illustrative embodiment. For example, flight control and high lift surfaces on at least one of wing 102 or wing 104 may use a load path status detection system.

As used herein, the phrase "at least one of," when used with a list of items, means different combinations of one or more of the listed items may be used, and only one of each item in the list may be needed. In other words, "at least one of" means any combination of items and number of items may be used from the list but not all of the items in the list are required. The item may be a particular object, thing, or a category.

For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A, one of item B, and ten of item C; four of item B and seven of item C; or other suitable combinations.

This illustration of aircraft 100 is provided for purposes of illustrating one environment in which the different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, a rotorcraft, or other suitable type of aircraft.

Although the illustrative examples for an illustrative embodiment are described with respect to an aircraft, an illustrative embodiment may be applied to other types of platforms. The platform may be, for example, a mobile platform, a stationary platform, a land-based structure, an aquatic-based structure, or a space-based structure. More specifically, the platform may be a surface ship, a tank, a personnel carrier, a train, a spacecraft, a space station, a satellite, a submarine, an automobile, a manufacturing facility, a building, or other suitable platforms.

Figure 2:
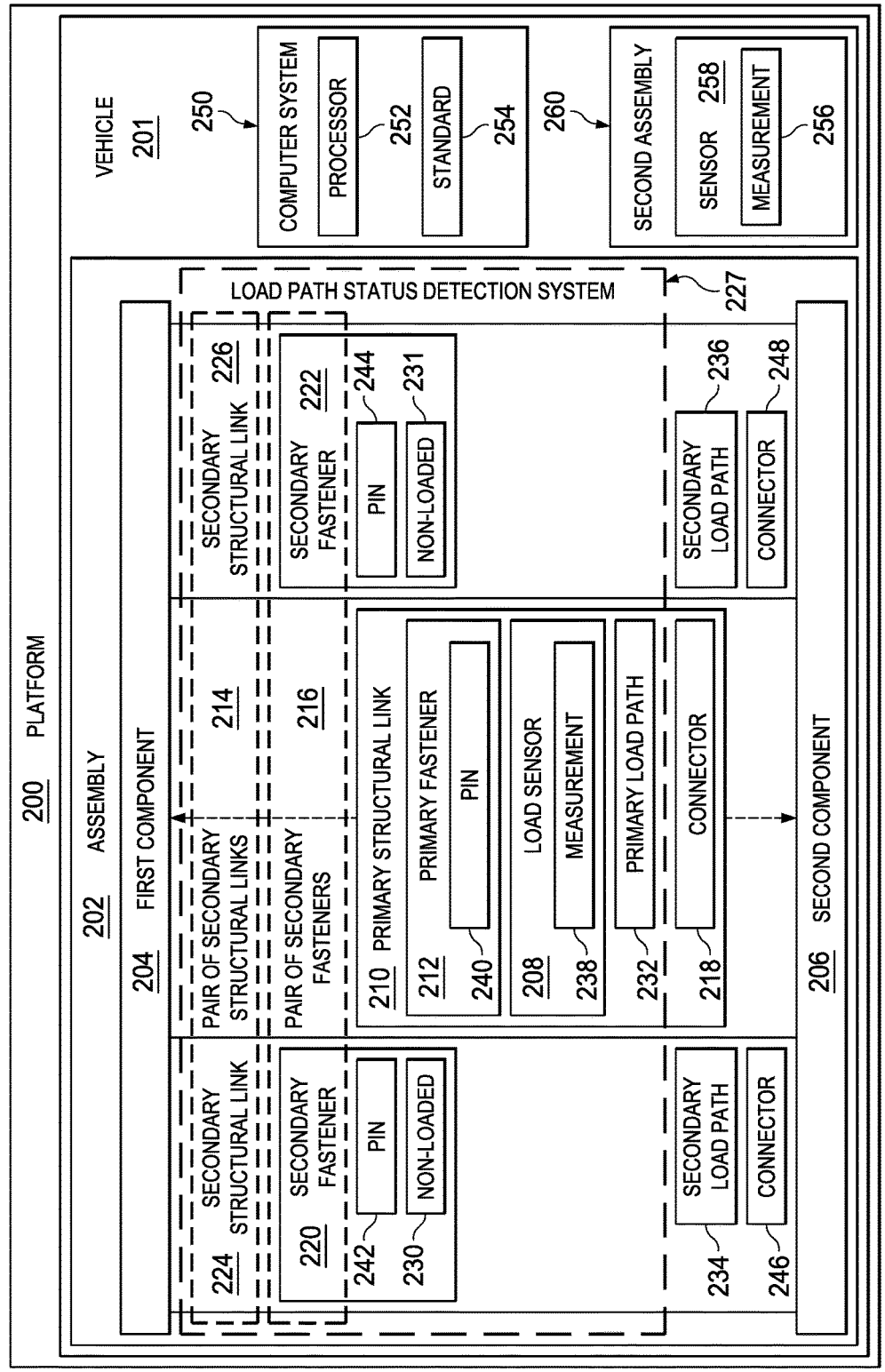
FIG. 2 is an illustration of a block diagram of a platform in accordance with an illustrative embodiment.

With reference now to FIG. 2, an illustration of a block diagram of a platform is depicted in accordance with an illustrative embodiment. In FIG. 2, platform 200 may be one implementation of the aircraft 100 in FIG. 1. In some illustrative examples, platform 200 may take the form of vehicle 201.

As depicted, assembly 202 of platform 200 includes first component 204, second component 206, and load sensor 208. First component 204 is connected to primary structural link 210 using primary fastener 212 and is connected to pair of secondary structural links 214 using pair of secondary fasteners 216.

Second component 206 is connected to primary structural link 210 using connector 218. Load sensor 208 is associated with primary structural link 210 and positioned to measure a load on primary structural link 210. Pair of secondary fasteners 216 does not carry a load when primary fastener 212 and primary structural link 210 are functioning. In some illustrative examples, a central axis of primary fastener 212 is parallel to and non-concentric with a central axis of each of pair of secondary fasteners 216.

Secondary fastener 220 of pair of secondary fasteners 216 is configured to be a back-up to primary fastener 212. Secondary fastener 222 of pair of secondary fasteners 216 is also configured to be a back-up to primary fastener 212. Secondary structural link 224 and secondary structural link 226 of pair of secondary structural links 214 are configured to be back-ups to primary structural link 210.

Load path status detection system 227 comprises primary fastener 212, load sensor 208, primary structural link 210, and secondary structural link 224. Primary fastener 212 extends through primary structural link 210. Load sensor 208 is associated with primary structural link 210.

When one component is "associated" with another component, the association is a physical association in the depicted examples. For example, a first component may be considered to be associated with a second component by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of, and/or an extension of the second component.

Primary structural link 210 carries a load when primary load path 232, formed by primary fastener 212 and primary structural link 210, is functioning. Secondary structural link 224 is parallel to primary structural link 210. Secondary structural link 224 does not carry a load when primary load path 232 is functioning.

Secondary fastener 220 and secondary fastener 222 do not carry a load when primary load path 232, formed by primary structural link 210 and primary fastener 212, is functioning. Thus, secondary fastener 220 is non-loaded 230 and secondary fastener 222 is non-loaded 231 during normal functioning. When primary structural link 210 and primary fastener 212 are functioning, the load extends through primary load path 232. Primary load path 232 extends through primary structural link 210.

When one of primary fastener 212 or primary structural link 210 is not functioning, the load extends through at least one of secondary load path 234 or secondary load path 236. Secondary load path 234 extends through secondary structural link 224 and secondary load path 236 extends through secondary structural link 226. The load is at least one of tension or compression. When at least one of primary structural link 210 or primary fastener 212 is not functioning, the load does not extend through primary structural link 210 or primary fastener 212.

In some illustrative examples, load sensor 208 is positioned within primary structural link 210. Load sensor 208 takes measurement 238 of a load in primary structural link 210. In some examples, load sensor 208 is at least one of a strain gauge, a linear variable differential transformer, or a hydrostatic sensor. Load sensor 208 is configured to detect at least one of tension or compression.

When primary structural link 210 and primary fastener 212 are functioning, measurement 238 will be greater than when either of primary structural link 210 or primary fastener 212 is not functioning. For example, when at least one of primary structural link 210 or primary fastener 212 is not functioning, measurement 238 is a half of the value or less of a measurement when primary fastener 212 is functioning. As another example, measurement 238 may be substantially zero when primary fastener 212 is not functioning.

In some illustrative examples, primary fastener 212 takes the form of pin 240. In some further examples, pin 240 is a fuse pin. In some illustrative examples, secondary fastener 220 takes the form of pin 242. In some further examples, pin 242 is a fuse pin. In some illustrative examples, secondary fastener 222 takes the form of pin 244. In some further examples, pin 244 is a fuse pin.

Pair of secondary fasteners 216 connects first component 204 to pair of secondary structural links 214. Connector 246 connects second component 206 to secondary structural link 224. Connector 248 connects second component 206 to secondary structural link 226.

Platform 200 also includes computer system 250. Computer system 250 includes processor 252 configured to compare measurement 238 from load sensor 208 to standard 254. Standard 254 is an expected value when primary load path 232, formed by primary structural link 210 and primary fastener 212, is functioning.

A difference between measurement 238 from load sensor 208 and standard 254 is determined. If the difference is within a set threshold, primary structural link 210 and primary fastener 212 are determined to be functioning. If the difference is outside a set threshold, at least one of primary structural link 210 or primary fastener 212 may not be functioning. An alert or other indication may be provided when the difference is outside the set threshold.

When the difference between measurement 238 and standard 254 is outside a threshold, measurement 238 may be compared to measurement 256. Because sensor 258 is positioned substantially the same with second assembly 260, as load sensor 208 is positioned within assembly 202, sensor 258 may be used for a confirmation of measurement accuracy of load sensor 208. Sensor 258 may act as a check in a number of checks to reduce or eliminate false positives for detecting when at least one of primary structural link 210 or primary fastener 212 stops functioning.

The illustration of platform 200 in FIG. 2 is not meant to imply physical or architectural limitations to the manner in which an illustrative embodiment may be implemented. Other components, in addition to or in place of the ones illustrated, may be used. Some components may be unnecessary. Also, the blocks are presented to illustrate some functional components. One or more of these blocks may be combined, divided, or combined and divided into different blocks when implemented in an illustrative embodiment.

For example, although processor 252 is shown as separate from load path status detection system 227, in other examples, processor 252 may be a component of load path status detection system 227. As another example, although only two sensors are shown, any quantity of sensors may be present. For example, each dual load path system in platform 200 may have an associated load path status detection system.

Further, although two secondary structural links are shown, any desirable number of secondary structural links may be present. For example, only one secondary structural link may be present in assembly 202. In another example, greater than two secondary structural links may be present in assembly 202.

Also, although two secondary fasteners are shown, fewer secondary fasteners may be present. For example, at least one of secondary fastener 220 or secondary fastener 222 may not be present. In this example, a single fastener may be associated with both secondary structural link 224 and secondary structural link 226. For example, secondary fastener 220 may be associated with both secondary structural link 224 and secondary structural link 226. Alternatively, secondary fastener 222 may be associated with both secondary structural link 224 and secondary structural link 226.

Figure 3:
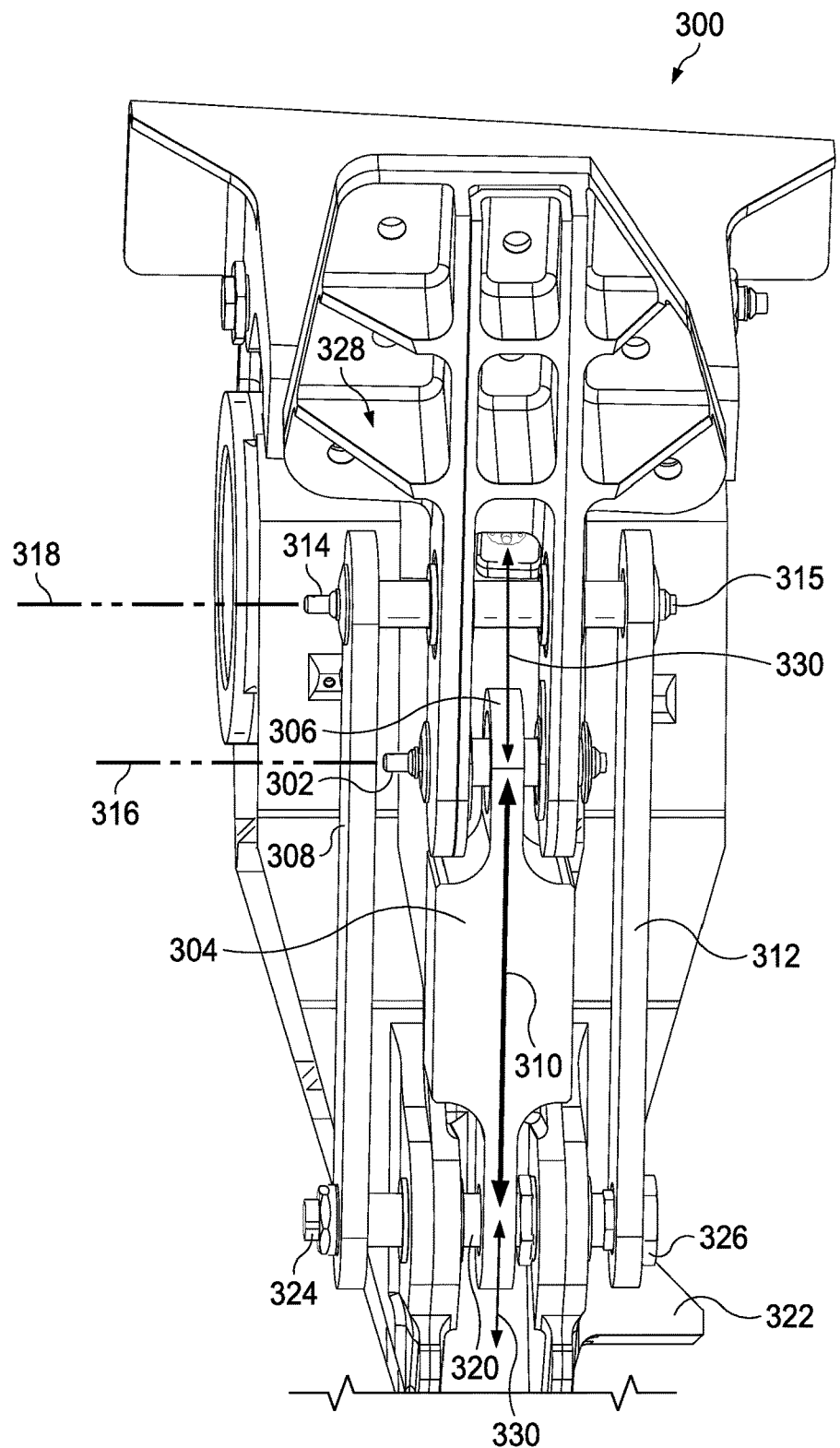
FIG. 3 is an illustration of a load path status detection system in accordance with an illustrative embodiment.

Turning now to FIG. 3, an illustration of a load path status detection system is depicted in accordance with an illustrative embodiment. Load path status detection system 300 is an example of a detection system used in aircraft 100 of FIG. 1. Load path status detection system 300 is a physical implementation of load path status detection system 227 of FIG. 2.

Load path status detection system 300 includes primary fastener 302, load sensor 304, primary structural link 306, and secondary structural link 308. Primary fastener 302 extends through primary structural link 306. Load sensor 304 is associated with primary structural link 306. Primary structural link 306 carries a load when primary load path 310, formed by primary fastener 302 and primary structural link 306, is functioning. Secondary structural link 308 is parallel to primary structural link 306. Secondary structural link 308 does not carry a load when primary load path 310 is functioning.

Secondary structural link 308 is a back-up for primary structural link 306. As depicted, load path status detection system 300 further comprises secondary structural link 312. Primary structural link 306 is positioned between secondary structural link 308 and secondary structural link 312.

Secondary fastener 314 extends through secondary structural link 308 and is configured to be a back-up for primary fastener 302. Secondary fastener 315 extends through secondary structural link 312 and is configured to be a back-up for primary fastener 302. As depicted, central axis 316 of primary fastener 302 is parallel to and non-concentric with central axis 318 of secondary fastener 314. In some other illustrative examples, central axis 316 of primary fastener 302 is parallel to and concentric with central axis 318 of secondary fastener 314.

As depicted, load sensor 304 is positioned within primary structural link 306. Load sensor 304 may take the form of one of a strain gauge, a linear variable differential transformer, or a hydrostatic sensor.

Connector 320 connects second component 322 to primary structural link 306. Connector 324 connects second component 322 to secondary structural link 308. Connector 326 connects second component 322 to secondary structural link 312.

Secondary fastener 314 connects secondary structural link 308 to first component 328. Secondary fastener 315 connects secondary structural link 312 to first component 328.

As depicted, load 330 on primary structural link 306 can be a tension or a compression load. As depicted, primary load path 310 is functioning. As a result, load 330 is carried by primary fastener 302 and primary structural link 306. More specifically, load 330 goes through primary load path 310.

Measurements taken by load sensor 304 in FIG. 3 would be compared to a standard. When primary fastener 302 is functioning, the difference between measurements taken by load sensor 304 and a standard should be within a threshold. When the difference between the measurements taken by load sensor 304 and a standard is within the threshold, primary fastener 302 and primary structural link 306 are determined to be functioning. When the difference between the measurements taken by load sensor 304 and a standard are outside the threshold, at least one of primary fastener 302 or primary structural link 306 is not functioning.

Figure 4:
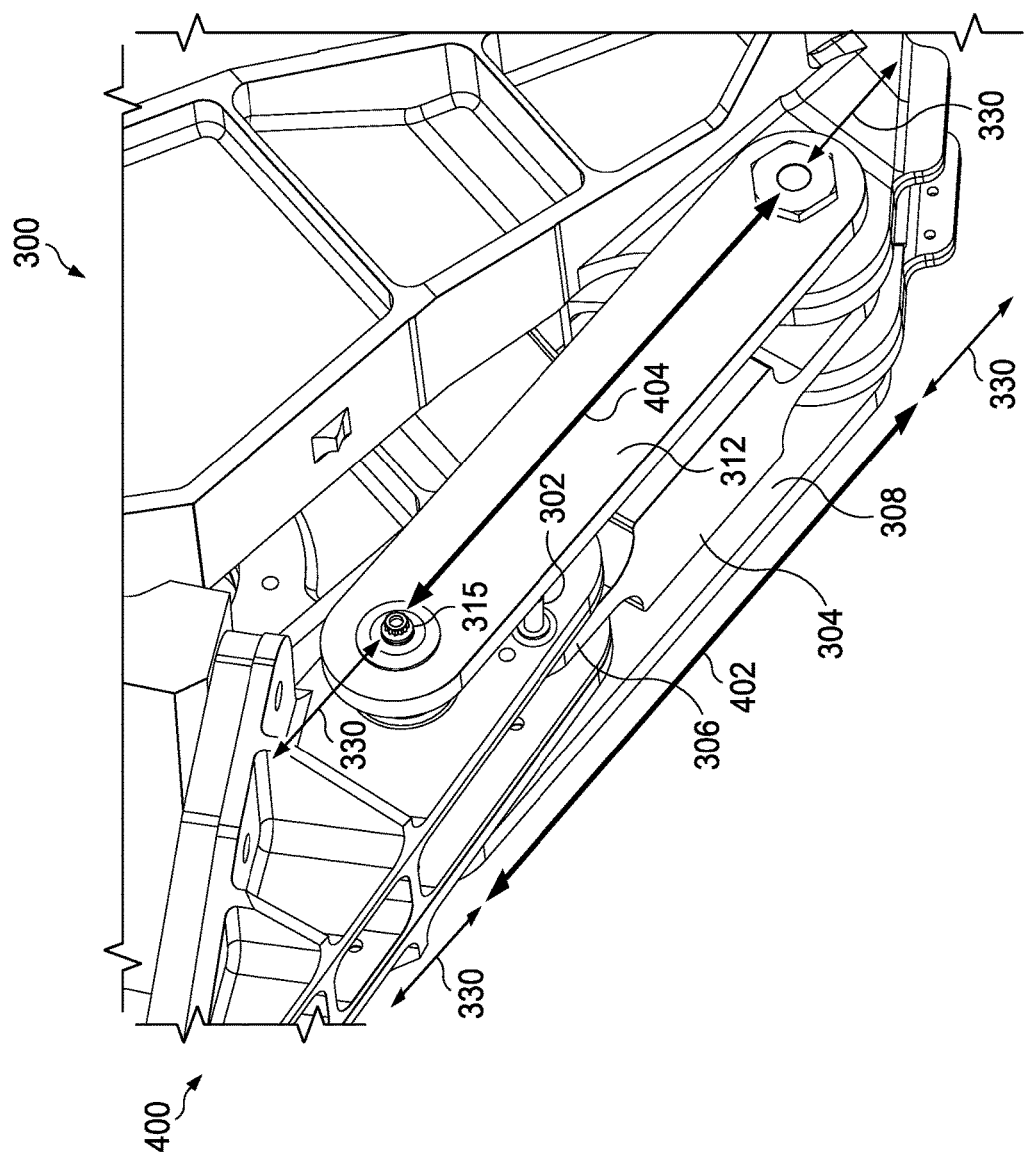
FIG. 4 is an illustration of a load path status detection system in accordance with an illustrative embodiment.

Turning now to FIG. 4, an illustration of a load path status detection system is depicted in accordance with an illustrative embodiment. View 400 is a view of load path status detection system 300 of FIG. 3, when at least one of primary fastener 302 or primary structural link 306 is not functioning.

In view 400, at least one of primary fastener 302 or primary structural link 306 is not functioning. Load 330 is carried by secondary structural link 308 and secondary structural link 312. Load 330 travels through secondary load path 402 and secondary load path 404. Primary load path 310 of FIG. 3 does not carry load in FIG. 4.

Measurements taken by load sensor 304 in FIG. 4 will be significantly lower than measurements taken by load sensor 304 in FIG. 3. Thus, a status of primary load path 310, formed by primary fastener 302 and primary structural link 306, is determined using measurements from load sensor 304. In some examples, measurements from load sensor 304 are compared to each other throughout use of load sensor 304, for example, during a flight. In another example, measurements from load sensor 304 are compared to a standard. In yet another example, measurements from load sensor 304 are compared to measurements taken from other sensors with substantially the same positioning.

The different components shown in FIG. 1 and FIGS. 3-4 may be combined with components in FIG. 2, used with components in FIG. 2, or a combination of the two. Additionally, some of the components in FIG. 1 and FIGS. 3-4 may be illustrative examples of how components shown in block form in FIG. 2 can be implemented as physical structures.

Figure 5:
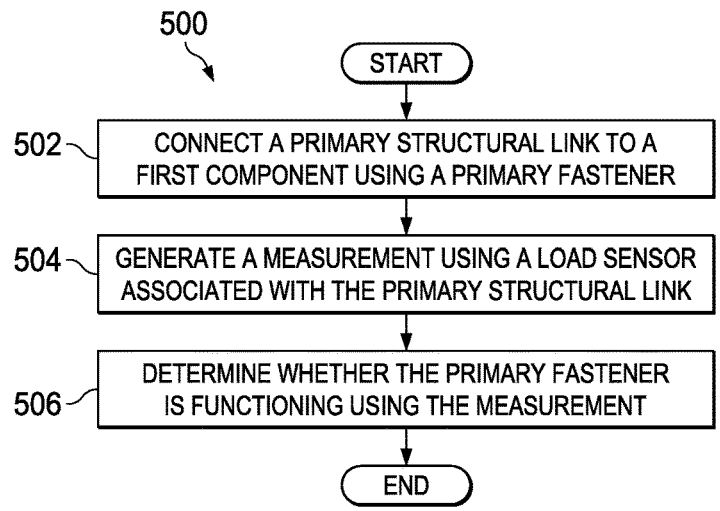
FIG. 5 is an illustration of a flowchart of a method for detecting load path status in accordance with an illustrative embodiment.

Turning now to FIG. 5, an illustration of a flowchart of a method for detecting load path status is depicted in accordance with an illustrative embodiment. Method 500 connects a primary structural link to a first component using a primary fastener (operation 502). Method 500 generates a measurement using a load sensor associated with the primary structural link (operation 504). The load sensor may be at least one of a strain gauge, a linear variable differential transformer, or a hydrostatic sensor. Method 500 determines whether the primary fastener is functioning using the measurement (operation 506). Afterwards the process terminates. In some illustrative examples, determining whether the primary load path is functioning using the measurement comprises determining if the measurement is outside a threshold. In these illustrative examples, method 500 may further comprise sending an alert if the measurement is outside the threshold.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, method 500 may further comprise carrying a load in a secondary structural link when the primary load path is not functioning. In other illustrative examples, method 500 may further comprise connecting the pair of secondary structural links to the first component using a pair of secondary fasteners, wherein a first load path extends through the primary structural link, and wherein a second load path extends through a pair of secondary structural links. In some illustrative examples, the primary structural link is positioned between the pair of secondary structural links.

Figure 6:
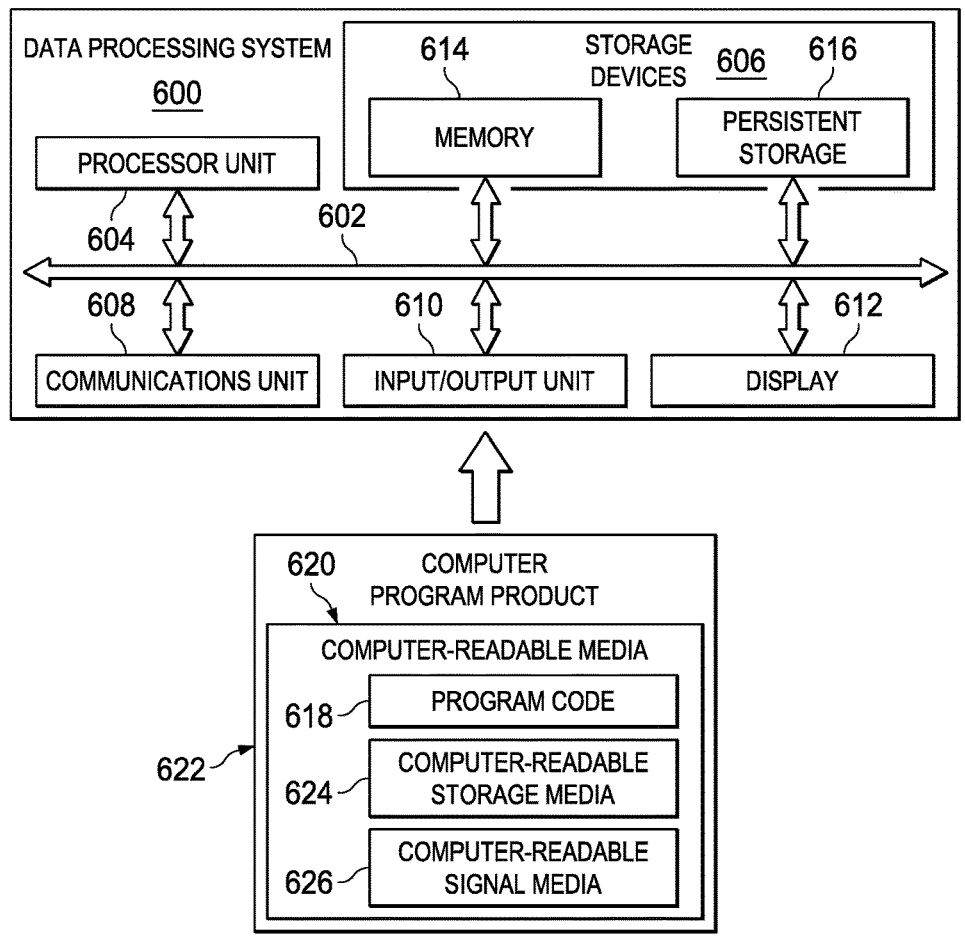
FIG. 6 is an illustration of a data processing system in the form of a block diagram in accordance with an illustrative embodiment.

Turning now to FIG. 6, an illustration of a data processing system in the form of a block diagram is depicted in accordance with an illustrative embodiment. Data processing system 600 may be used to implement processor 252 of FIG. 2. Data processing system 600 may be used to process data, such as measurements from load sensor 304 of FIG. 3. As depicted, data processing system 600 includes communications framework 602, which provides communications between processor unit 604, storage devices 606, communications unit 608, input/output unit 610, and display 612. In some cases, communications framework 602 may be implemented as a bus system.

Processor unit 604 is configured to execute instructions for software to perform a number of operations. Processor unit 604 may comprise a number of processors, a multi-processor core, and/or some other suitable type of processor, depending on the implementation. In some cases, processor unit 604 may take the form of a hardware unit, such as a circuit system, an application specific integrated circuit (ASIC), a programmable logic device, or some other suitable type of hardware unit.

Instructions for the operating system, applications, and/or programs run by processor unit 604 may be located in storage devices 606. Storage devices 606 may be in communication with processor unit 604 through communications framework 602. As used herein, a storage device, also referred to as a computer readable storage device, is any piece of hardware capable of storing information on a temporary and/or permanent basis. This information may include, but is not limited to, data, a program code, and/or other information.

Memory 614 and persistent storage 616 are examples of storage devices 606. Memory 614 may take the form of, for example, a random access memory or some type of volatile or non-volatile storage device. Persistent storage 616 may comprise any number of components or devices. For example, persistent storage 616 may comprise a hard drive, a flash memory drive, a rewritable optical disk, a rewritable magnetic tape, or some combination of the above. The media used by persistent storage 616 may or may not be removable.

Communications unit 608 allows data processing system 600 to communicate with other data processing systems and/or devices. Communications unit 608 may provide communications using physical and/or wireless communications links.

Input/output unit 610 allows input to be received from, and output to be sent to other devices connected to data processing system 600. For example, input/output unit 610 may allow user input to be received through a keyboard, a mouse, and/or some other type of input device. As another example, input/output unit 610 may allow output to be sent to a printer connected to data processing system 600.

Display 612 is configured to display information to a user. Display 612 may comprise, for example, without limitation, a monitor, a touch screen, a laser display, a holographic display, a virtual display device, and/or some other type of display device.

In this illustrative example, the processes of the different illustrative embodiments may be performed by processor unit 604 using computer-implemented instructions. These instructions may be referred to as a program code, a computer usable program code, or a computer readable program code, and may be read and executed by one or more processors in processor unit 604.

In these examples, program code 618 is located in a functional form on computer-readable media 620, which is selectively removable, and may be loaded onto or transferred to data processing system 600 for execution by processor unit 604. Program code 618 and computer-readable media 620 together form computer program product 622. In this illustrative example, computer-readable media 620 may be computer-readable storage media 624 or computer-readable signal media 626.

Computer-readable storage media 624 is a physical or tangible storage device used to store program code 618, rather than a medium that propagates or transmits program code 618. Computer-readable storage media 624 may be, for example, without limitation, an optical or magnetic disk, or a persistent storage device that is connected to data processing system 600.

Alternatively, program code 618 may be transferred to data processing system 600 using computer-readable signal media 626. Computer-readable signal media 626 may be, for example, a propagated data signal containing program code 618. This data signal may be an electromagnetic signal, an optical signal, and/or some other type of signal that can be transmitted over physical and/or wireless communications links.

The illustration of data processing system 600 in FIG. 6 is not meant to provide architectural limitations to the manner in which the illustrative embodiments may be implemented. The different illustrative embodiments may be implemented in a data processing system that includes components in addition to or in place of those illustrated for data processing system 600. Further, components shown in FIG. 6 may be varied from the illustrative examples shown.

Figure 7:
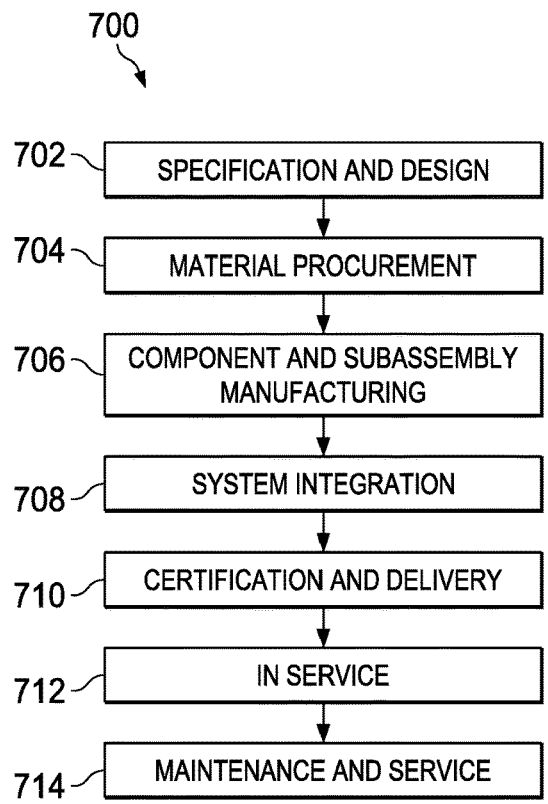
FIG. 7 is an illustration of an aircraft manufacturing and service method in the form of a block diagram in accordance with an illustrative embodiment.
Figure 8:
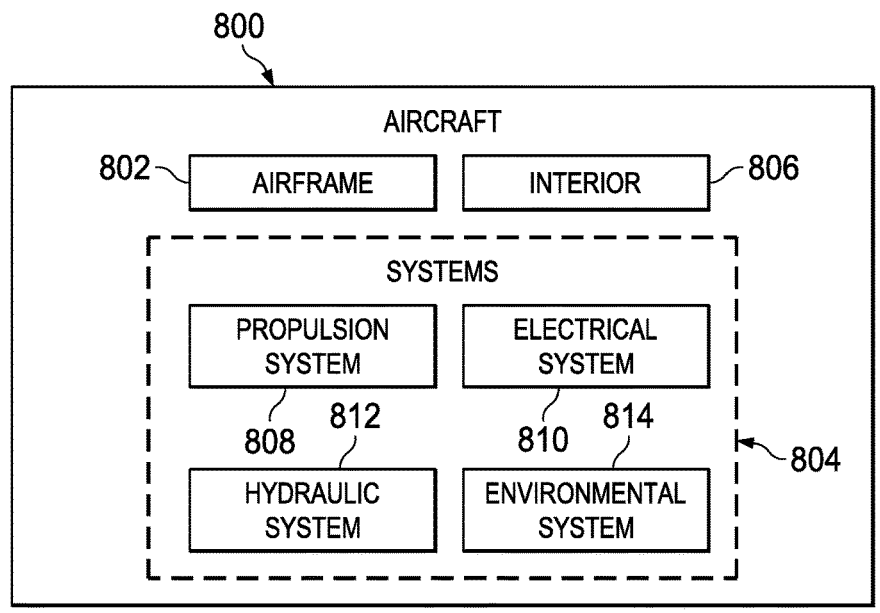
FIG. 8 is an illustration of an aircraft in the form of a block diagram in which an illustrative embodiment may be implemented.

Illustrative embodiments of the disclosure may be described in the context of aircraft manufacturing and service method 700 as shown in FIG. 7 and aircraft 800 as shown in FIG. 8. Turning first to FIG. 7, an illustration of an aircraft manufacturing and service method is depicted in accordance with an illustrative embodiment. During preproduction, aircraft manufacturing and service method 700 may include specification and design 702 of aircraft 800 in FIG. 8 and material procurement 704.

During production, component and subassembly manufacturing 706 and system integration 708 of aircraft 800 in FIG. 8 takes place. Thereafter, aircraft 800 in FIG. 8 may go through certification and delivery 710 in order to be placed in service 712. While in service 712 by a customer, aircraft 800 in FIG. 8 is scheduled for routine maintenance and service 714, which may include modification, reconfiguration, refurbishment, or other maintenance and service.

Each of the processes of aircraft manufacturing and service method 700 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, or suppliers; and an operator may be an airline, a leasing company, a military entity, a service organization, and so on.

With reference now to FIG. 8, an illustration of an aircraft is depicted in which an illustrative embodiment may be implemented. In this example, aircraft 800 is produced by aircraft manufacturing and service method 700 in FIG. 7 and may include airframe 802 with a plurality of systems 804 and interior 806. Examples of systems 804 include one or more of propulsion system 808, electrical system 810, hydraulic system 812, and environmental system 814. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 700 in FIG. 7. One or more illustrative embodiments may be used during component and subassembly manufacturing 706. For example, load sensor 208 in FIG. 2 may be installed relative to a primary structural link during component and subassembly manufacturing 706. Further, measurement 238 from load sensor 208 is used to determine if primary fastener 212 or primary structural link 210 should be replaced during maintenance and service 714.

The illustrative embodiments provide a method and apparatus for determining a status of a fastener. More specifically, the illustrative embodiments provide a method and apparatus for determining if a primary fastener is still functioning.

A method to assess the integrity of a structure is presented. A sensor such as a strain gauge, a linear variable differential transformer (LVDT) sensor, or a hydrostatic sensor is placed along a primary structural link. In some examples, the primary structural link is a primary tension link. The load is carried through the primary structural link and primary fastener during normal conditions. The secondary fastener is non-load bearing, except in the case of a primary load path comprising the primary fastener and the primary structural link not functioning properly. The sensor reading taken will be indicative of whether the primary load path is carrying the load. When the primary load path is not carrying the load, at least one of a primary structural link malfunction or a primary fastener malfunction is indicated.

Readings from a sensor may be compared to readings from other sensors. For example, when the load path status detection system is installed on an aircraft, such as on flight control surfaces, the readings can be compared between the left and the right wing, and between supports common to a flight control surface to confirm the drop in strain is due to primary fastener malfunction.

When integrity of the primary fastener is compromised, a sensor, such as load sensor 208, detects a non-loaded portion value. The value may be predetermined. In some examples, a measurement between 0 and a little under half of a loaded value may indicate primary load path 232 is not carrying the load. Any known method (electrical signal, wireless, etc.) can be used to transfer the measurement to the maintenance log. The maintenance crew, during routine checks, can determine if the primary fastener is functioning by checking the value in their maintenance log. Checking the value may be at least one of less difficult or less time-consuming than checking conventional detection methods, such as spring-loaded doors.

The disclosed load path status detection system may save weight on an aircraft. For example, a sensor, such as load sensor 208 in FIG. 2, may weigh less than a mechanical detection system, such as a spring-loaded window. Further, the disclosed load path status detection system may produce a cost savings. For example, the disclosed load path status detection system may reduce maintenance costs by reducing false positive failure results. The disclosed load path status detection system also has increased reliability over conventional mechanical detection systems.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A load path status detection system comprising:
 a primary fastener extending through a primary structural link;
 a load sensor associated with the primary structural link;
 the primary structural link that carries a load when a primary load path formed by the primary fastener and the primary structural link is functioning; and
 a secondary structural link parallel to the primary structural link, wherein the secondary structural link does not carry the load when the primary load path is functioning.

2. The load path status detection system of claim 1 further comprising:
 an additional secondary structural link, wherein the primary structural link is positioned between the secondary structural link and the additional secondary structural link.

3. The load path status detection system of claim 1 further comprising:
 a secondary fastener extending through the secondary structural link and configured to be a back-up to the primary fastener.

4. The load path status detection system of claim 3, wherein a central axis of the primary fastener is parallel to a central axis of the secondary fastener.

5. The load path status detection system of claim 4, wherein the central axis of the primary fastener is concentric with the central axis of the secondary fastener.

6. The load path status detection system of claim 1, wherein the load sensor is positioned within the primary structural link.

7. The load path status detection system of claim 1, wherein the load sensor is at least one of a strain gauge, a linear variable differential transformer, or a hydrostatic sensor.

8. A method comprising:
 connecting a primary structural link to a first component using a primary fastener to form a primary load path;
 generating a measurement using a load sensor associated with the primary structural link; and
 determining whether the primary load path is functioning using the measurement.

9. The method of claim 8 wherein determining whether the primary load path is functioning using the measurement comprises determining if the measurement is outside a threshold, and the method further comprising:
 sending an alert if the measurement is outside the threshold.

10. The method of claim 8 wherein the load sensor is at least one of a strain gauge, a linear variable differential transformer, or a hydrostatic sensor.

11. The method of claim 8 further comprising:
 connecting a pair of secondary structural links to the first component using a pair of secondary fasteners, wherein a first load path extends through the primary structural link, and wherein a second load path extends through a pair of secondary structural links.

12. The method of claim 11 wherein the primary structural link is positioned between the pair of secondary structural links.

13. The method of claim 8 further comprising:
 carrying a load in a secondary structural link when the primary load path is not functioning.

14. An assembly comprising:
 a first component connected to a primary structural link using a primary fastener and connected to a pair of secondary structural links using a pair of secondary fasteners;
 a second component connected to the primary structural link using a connector; and
 a load sensor associated with the primary structural link and configured to measure a load on the primary structural link.

15. The assembly of claim 14, wherein the pair of secondary fasteners does not carry a load when the primary fastener and the primary structural link are functioning.

16. The assembly of claim 15 wherein a central axis of the primary fastener is parallel to a central axis of each of the pair of secondary fasteners.

17. The assembly of claim 14 wherein the load sensor is at least one of a strain gauge, a linear variable differential transformer, or a hydrostatic sensor.

18. The assembly of claim 14 wherein the load is selected from one of tension or compression.

19. The assembly of claim 14 wherein a first load path extends through the primary structural link and wherein a second load path extends through the pair of secondary structural links.

* * * * *